(12) United States Patent
Buchheit (10) Patent No.: US 8,605,082 B2
(45) Date of Patent: Dec. 10, 2013

(54) RENDERING ADJUSTMENTS TO AUTOCOMPENSATE FOR USERS WITH OCULAR ABNORMALITIES

(76) Inventor: Brian K. Buchheit, Weston, FL (US)

(*) Notice: Subject to any disclaimer, the term of this patent is extended or adjusted under 35 U.S.C. 154(b) by 367 days.

(21) Appl. No.: 13/088,598

(22) Filed: Apr. 18, 2011

(65) Prior Publication Data

US 2012/0262477 A1    Oct. 18, 2012

(51) Int. Cl.
*G06T 15/00* (2011.01)
*G09G 5/00* (2006.01)

(52) U.S. Cl.
USPC ............................ 345/419; 345/619; 345/643

(58) Field of Classification Search
None
See application file for complete search history.

(56) References Cited

U.S. PATENT DOCUMENTS

| 8,218,061 | B2* | 7/2012 | Baxansky | 348/345 |
| 2002/0180733 | A1* | 12/2002 | Colmenarez et al. | 345/427 |
| 2009/0231355 | A1* | 9/2009 | Perronnin | 345/594 |
| 2011/0157180 | A1* | 6/2011 | Burger et al. | 345/428 |

* cited by examiner

*Primary Examiner* — Kee M Tung
*Assistant Examiner* — Leon T Cain, II
(74) *Attorney, Agent, or Firm* — Brian K. Buchheit; Scott M. Garrett; Patents on Demand, P.A.

(57) ABSTRACT

A digital screen rendering resolution adjustment can allow users who are conventionally dependent upon corrective lenses to view the digital screen to, after the resolution adjustment, view the contents of this screen with 20×20 vision (considered normal vision), without the use of these corrective lenses. A linear algebraic transform (performing essentially the inverse of the Lensmaker's Equation) can be applied and enact matrix manipulation that when rendering the graphical display to autocompensate for a viewer's visual abnormalities, can result in a distorted screen that is equivalent to the inverse of a corrective lens prescription. A screen rendering customization to autocompensate for a user's visual impairment can be applied for each eye in 3D capable devices due to the inherent nature of 3D to display separate images per eye. A unique algebraic transform matrix manipulation can be performed for each of the two images and can provide a more exact corrective lens prescription rendering simulation than for single image rendering for a display.

18 Claims, 5 Drawing Sheets

RENDERING ADJUSTMENTS TO AUTOCOMPENSATE FOR USERS WITH OCULAR ABNORMALITIES

BACKGROUND

The field of the disclosure is the field of electronic displays, and more particularly digital displays with resolution adjustment capabilities.

Many individuals have eye conditions that can make navigating through their daily life difficult without the aid of corrective lenses (e.g., glasses or contact lenses). This is especially evident when considering how much of modern daily life is spent viewing devices with digital displays, which compound eye strain due to their very nature.

Following are some examples of daily tasks or activities that glasses or contact lens wearers may find challenging: upon waking, being able to read digital time displays without the aid of glasses or contact lenses; falling asleep while watching television, resulting in glasses that may have damaged or bended frames the next morning; falling asleep while watching television, wearing contact lenses that still need to be removed for the health of the eye; neglecting to bring reading glasses to work, resulting in an inability to read from and work on a computer; losing or tearing a contact lens, resulting in an inability to read from and work on a computer.

Additionally, technology advances in the realm of commercially available 3D capable electronic consumer devices require the use of specialized glasses to view these 3D effects in their intended fashion. For users with visual abnormalities, such glasses would need to be worn on top of their already prescribed corrective lenses. Prescription 3D glasses can allow the user to only have to wear a single set of lenses to compensate for visual abnormalities as well as allowing proper viewing of three dimensional 3D content. However, these glasses can be extremely expensive, even so far as to be a preventative cost.

SUMMARY

One embodiment of the disclosure presents a tool for allowing a digital screen resolution adjustment that makes it possible to adjust for a user's ocular abnormality. An algebraic transform (performing essentially the inverse of the lens maker's equation) can be applied when rendering the graphical display to autocompensate for a viewer's visual abnormalities. After the resolution adjustment, users who are conventionally dependent upon corrective lenses to view the digital screen, can then view the electronic display without his or her corrective lenses with what is effectively 20×20 vision (considered normal vision).

In another embodiment, the disclosure can allow for left and right eye specific rendering adjustments in 3D capable devices. The inherent nature of 3D to display separate images per eye to create the perception of depth can allow for a more tailored customized screen. That is, the embodiment of the disclosure can account for cases where users have differing levels of ocular abnormality in each eye. A unique algebraic transform can be applied for each eye's designated image of the stereographic technique in creating a 3D visual media presented on an electronic display. Thus a user can forego the expensive purchase of prescription 3D glasses.

In yet another embodiment of the disclosure, a system for sharing user specific rendering adjustment preferences can be utilized. This implementation of the innovative arrangements disclosed herein can allow various eligible devices to have access to previously established user display customization preferences. In such a manner these various devices can auto compensate for a user's visual abnormality in a seamless fashion from the perspective of the user. He or she can forego the task of "programming" each device with the correct desired display settings.

DETAILED DESCRIPTION

Assistive technologies facilitating the use of consumer electronic devices due to the fact that they compensate for a user's handicaps exist for such handicaps as hearing loss, full vision loss, motor disabilities, and the like. Full vision loss is not the same, however, as an individual suffering from visual abnormalities. Conventionally, visual abnormalities are not considered a handicap until reaching a status considered "legally blind". However, eye disorders affecting eyesight at a level lower than this can also be debilitating to a user of electronic consumer devices without the proper corrective lens.

Prevalent eye disorders are, for example, myopia (near-sightedness), hyperopia (far-sightedness), astigmatism (blurred vision), presbyopia (vision loss symptoms/inability to focus on near objects due to advanced age), color blindness (inability to perceive differences between some colors) and the like. These eye conditions are able to be corrected for due to the fact that they are accommodation and refractive disorders of the eye, with the exception of color blindness which is classified as a visual disturbance or blindness and does not have a common "fix".

Specialized corrective lenses (for example eye glasses or contact lenses—in either a divergent or convergent shape depending on eye condition) may be prescribed to aid a person with certain accommodation and refractive eye disorders in driving, reading, watching television, seeing his or her alarm clock, and other activities. These corrective lenses work by bending incoming light to the eye thereby adjusting the focal point to where an individual's eyes focus an image once it reaches the retina (not before or after). It should be noted that suffering from one of these disorders does not preclude one from suffering from other eye diseases. A person may suffer from far-sightedness as well as astigmatism, or, for example due to advanced age, also near-sightedness. Of course, any corrective lenses need to be worn at times fully corrected vision is desired, regardless of time of day or circumstance.

In determining the proper prescription for individuals with compromised vision, optometrists and ophthalmologists gauge a person's ability to see objects in comparison to what other individuals see clearly from 20 feet away (20×20 vision is considered normal). The Lensmaker's Equation (an algebraic formula) is then utilized to manufacture the appropriate lens to compensate for the user's specific eye disorder and the magnitude of its effect on his or her vision.

This disclosure presents a system, method, or computer program product for recreating the Lensmaker's Equation's effect on an individual's eyesight via a specially constructed corrective lens with the task to bend light in the necessary direction on a digital display. Applying an algebraic transform to the rendering process of a screen of an electronic consumer device via its graphics card and processor unit can achieve an effect that is essentially the inverse of a user putting on a set of glasses. In such a fashion, light can be bent directly coming off the screen compensating for the user's abnormal focal point.

Devices with digital screens whose rendering and display resolution can be adjusted in accordance with an embodiment of the disclosure are, for example, computer monitors, laptop screens, mobile phone screens, tablet screens (such as IPADs and Android tablets), digital media players (such as IPODS, portable DVD players, in-vehicle DVD players), GPS units and radios, and the like), e-ink reader screens (such as NOOK and KINDLE screens, etc.), digital alarm clock screens, televisions (for example, LCD, plasma, LED), remote controls with screens, SMARTHOUSE or SMARTHOME operation screens, teleprompters and the like.

With the widespread availability and lower costs of such devices, their pervasive incorporation into users' lives, even at times when a user's vision may be compromised due to a variety of factors, is inevitable. Conventional displays have multiple options for displaying screen content. Generally, this screen resolution rendering via the graphics engine, which is measured in pixels both horizontally and vertically, can be controlled in a user friendly manner through the respective computer device's operating system (more specifically, a control panel function or the like). Display resolution and the device's resolution adjustment capabilities will vary per device based on its specific video card device(s), monitor or screen size, and video and monitor/screen drivers.

Each screen device configuration will have a recommended display option against which other resolutions can be compared. Overall, at lower resolution options fewer but larger items will fit on the available screen. Vice versa, when increasing screen resolution, more items that are, however, smaller can be displayed. Sharpness of objects on the screen is determined by the screen resolution in that the higher the screen resolution is, the sharper the object appears. Users can choose their own preferences for viewing the screen. However, these conventionally available user preference adjustments for screen resolution do not adjust for a user's potential corrective lens use; they do not allow the user to view the screen clearly and without difficulty with 20×20 vision without the use of any potentially prescribed corrective lenses.

As will be appreciated by one skilled in the art, aspects of the present invention may be embodied as a system, method or computer program product. Accordingly, aspects of the present invention may take the form of an entirely hardware embodiment, a software embodiment (including firmware, resident software, micro-code, etc.) where the software embodiment can include a storage medium (which can be a tangible, physical, non-transitory storage medium) within which the software resides, or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer program stored on a computer readable storage medium may be propagated over a distance via a computer readable signal medium.

The computer readable storage medium can be a tangible, non-transitory medium. The computer readable storage medium can be a physical device or part of a physical device in which information is digitally encoded. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 1:
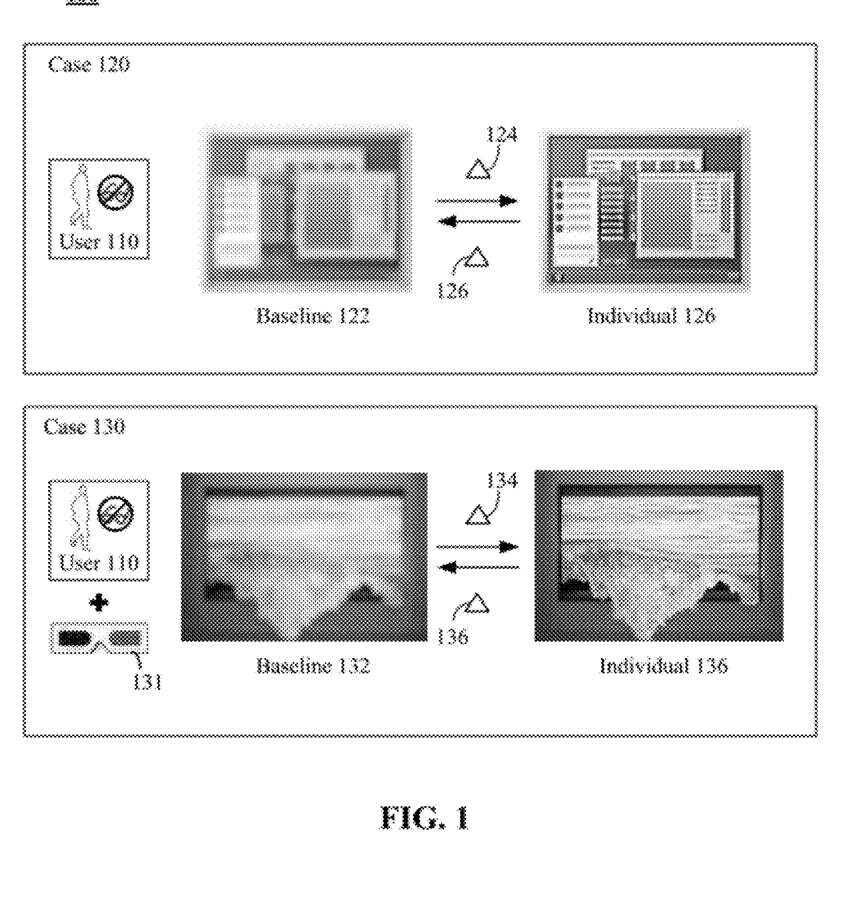
FIG. 1 shows a set of use cases in accordance with an embodiment of the inventive arrangements disclosed herein.

FIG. 1 shows a set of use cases in accordance with an embodiment of the inventive arrangements disclosed herein. Cases 120, 130 are intended to give an overview of the disclosure and are for illustrative purposes; they are not intended to be limiting. More specifically, cases 120, 130 can show that regardless of electronic consumer device specifics (an example of which is addressed in FIG. 2), the disclosure can be implemented, as long as the device includes a digital display with a decent resolution (which has become mainstream on devices such as GPS units, smartphones, tablets, IPOD docks, etc.), which can be manipulated for example at a low-level, including but not limited to, at a kernel or firmware level, or receive customized video drivers, very little hardware modification has to occur.

It should be noted that in one embodiment implementing a software module for adjusting screen resolution in accordance with the disclosure below the operating system (OS) layer can give the benefit of allowing each user of the machine to have his or her own resolution settings, something not conventionally possible. In fact, Windows 7 does not allow each user his or her own settings; rather, changing resolution on the machine affects all user accounts until resolution is changed again.

As case 120 shows, user 110, who is conventionally dependent upon viewing his or her environment with the aid of corrective lenses, be they glasses or contact lenses, etc., viewing a digital display without his or her corrective lenses. Baseline 122 monitor and display screen indicate the blurry vision an individual has of the display when the image on the display is rendered in a conventional manner.

Applying an algebraic transform (delta 124) to the rendering algorithms for constructing the image displayed on the digital screen, in accordance with one embodiment of the disclosure, individual display 126 results in a clearly visible (as if viewing the screen with 20×20 vision, considered normal) without the aid of corrective lenses. To an individual with natural 20×20 vision, the individualized display 126 of user 110 can look as if viewing the display through user 110's prescription glasses—distorted. Removing the linear algebraic matrix manipulation (delta 126) will revert the screen rendering resolution to baseline 122 display.

One fact of note is that in case 120 only one user specific eye can "be adjusted for"; for individuals who have differing magnitudes of visual abnormalities in each eye (the majority of individuals with eye disorders) the algebraic transform can account for one eye, but not the other at the same time. For most users 110 this would not present a difficulty, however, for two reasons: visual differences between two eyes are generally minor and the human brain can compensate fairly easily for these minor differences.

Case 130 illustrates an application of the customized rendering adjustment autocompensating for a user 110's visual abnormalities on 3D capable devices. User 110 can view baseline 132 display (conventional rendering of images displayed) without his or her corrective lenses and with a specialized set of 3D glasses that have two different lenses that filter a specific image to be viewed per eye. Without both the user 110's prescription corrective lenses as well as 3D glasses 131, the user cannot view the media/images displayed as designed. Presently, he or she can purchase prescription 3D glasses as 3D technology is becoming more pervasive (e.g., through commercially available 3D capable televisions and monitors). However, these prescription 3D glasses can be very expensive as some basic (i.e., non-prescription) 3D glasses are already costly without customized prescription lenses.

On 3D capable devices (including, but not limited to, stereographic devices as well as devices utilizing anaglyph images emulating a stereographic effect on a single monitor, and the more advanced "glasses free" autostereoscopy capable devices), rendering adjustment (delta 134) in accordance with one embodiment of the disclosure can be applied on an eye specific basis due to 3D's inherent nature of displaying a specific image per eye to create the visual appearance of depth (a third dimension). This can lead to user 110 being able to see the screen of an electronic consumer device in 3D clearly (with 20×20 vision) without the use of his her corrective lenses, but solely with 3D glasses 131; the image displayed after rendering adjustments is a perfectly user-specific customized one, meaning that for an individual with each eye having a differing level of visual abnormality, each eye's visual needs can be compensated for. In another embodiment of the disclosure, due to the nature of 3D devices displaying two images at the same time and the glasses filtering the incoming image per eye, it can also be possible for two individuals with the need for corrective lenses of differing prescription to view two separate images or videos in 2D (for example, these separate images or videos can be the same show or different show for each user) on the same 3D enabled device.

It should be noted that an additional benefit arising from the use of an embodiment of the disclosure can be a certain level of security. With a user's device's display having user-specific rendering adjustments it can be difficult for other individuals with perfect 20×20 vision or a differing level of visual abnormalities than the user to view the user's device clearly (for some individuals it may even be impossible to decipher what is displayed on the screen). Of course for individuals with similar vision adjustment needs than the device's user this would not apply as a benefit as these individuals would be able to view the screen in a similar clarity as the initial user.

Figure 2:
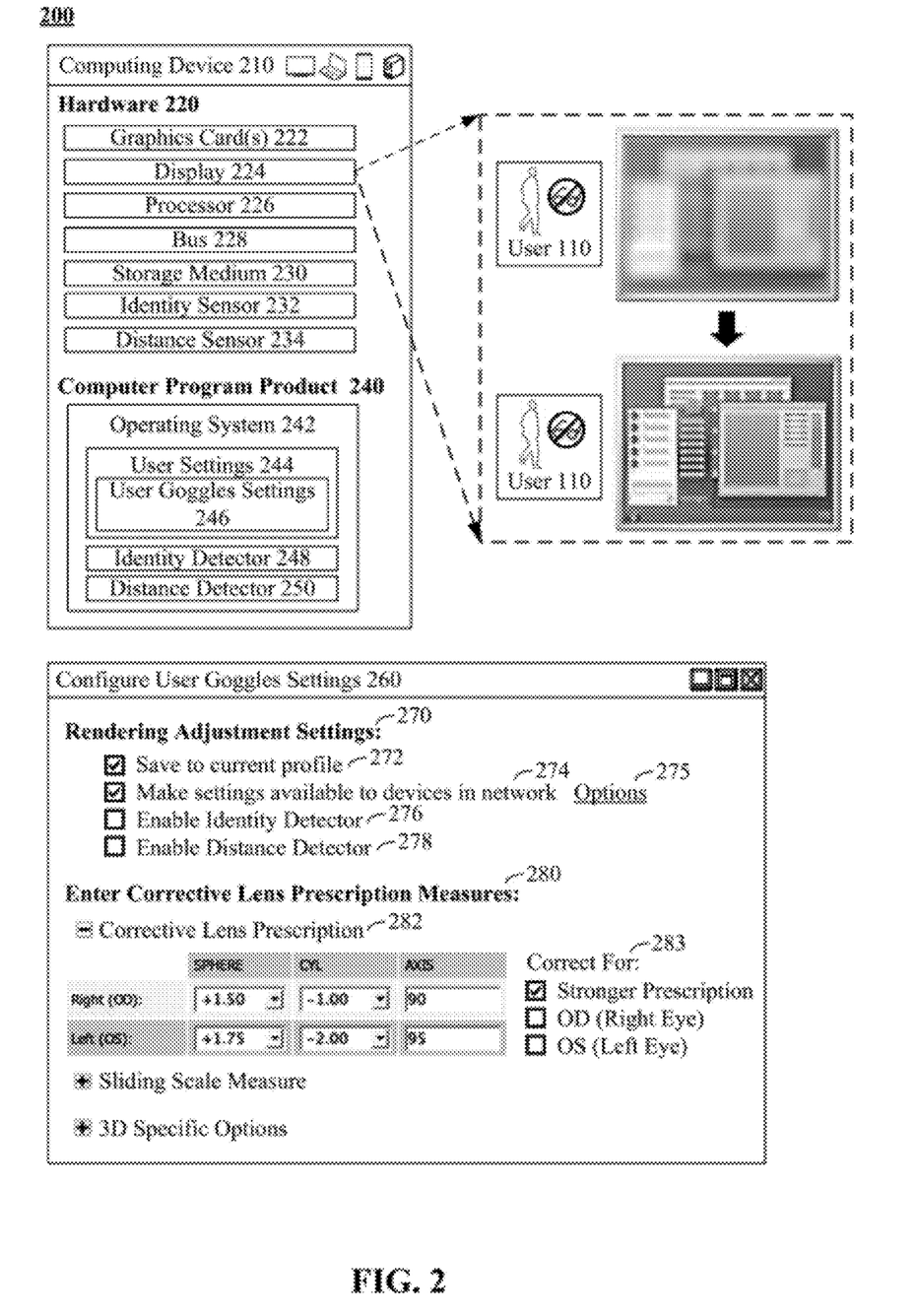
FIG. 2 shows a schematic diagram of a system for adjusting digital screen resolution for users with refractive or accommodation eye disorders, along with a user interface for entering preferences based on, for example, an ophthalmologist prescription for corrective lenses, for the digital screen resolution adjustment in accordance with an embodiment of the inventive arrangements disclosed herein.

FIG. 2 shows a schematic diagram of a system for adjusting digital screen resolution for users with refractive or accommodation eye disorders along with a user interface for entering preferences based on, for example, an ophthalmologist prescription for corrective lenses, for the digital screen resolution adjustment in accordance with an embodiment of the inventive arrangements disclosed herein.

System 200 shows a computing device 210 that includes hardware 220 and one or more computer program products 240. The computing device 210 can be any apparatus or device having a display screen capable of having screen resolution adjustments. The computing device 210 can be, but is not limited to, a personal computer, a smart phone, a media player, a kiosk, a gaming system, a navigation system, and the like. Device 210 can be a general purpose computing device able to have its functionality modified by updating or changing installed applications, can be a special purpose computing device designed for a specific set of functionality that is not user modifiable (or minimally so, such as through a firmware upgrade), or can be a device with an intermediate level of user modifiability (i.e., plug-ins or apps can be installed by a user who is otherwise not able to modify core functionality of the device).

The hardware 220 can include one or more processors 226 able to execute programmatic instructions of one or more computer program products 240. The processor 226 can be connected to other hardware 220 components, which include storage medium 230, via a bus 228. Storage medium 230 can be a non-transitory storage medium, such as a hard drive, Random Access Memory (RAM), a solid state drive, an optical storage medium (DVD disk, BLU-RAY disk), and the like. Hardware 220 can include ports for interacting with external output (e.g., display 224) components or can include one or more embedded or integrated output components (display 224).

Display 224 can be an output device capable of being subject to and displaying customizable rendering adjustments clearly as described by the disclosure. The display 224 can be active or passive and can use a digital or analog input signal depending on implementation specifics. Common display 224 types include Liquid Crystal Displays (LCDs) Cathode Ray Tube displays (CRTs), Organic Light Emitting Diode (OLED) displays, video projector displays, e-ink displays (e.g., field emission display), electronic paper displays, and the like. After implementation of the current disclosure, user 110 can view display 224 with clear 20×20 vision without the use of his or her corrective lenses, which before would have resulted in a blurred view of the display, as will still be the result for anything except the auto compensated display 224.

Hardware 220 can also include one or more graphics card(s) 222 responsible for presenting rendered images on display 224. Graphics Card(s) 222 can be integrated on the motherboard or one or more expansion cards. More specifically, graphics card(s) 222 can also be a video card, video adapter, graphics accelerator card, display adapter, a hybrid card, an integrated graphics processing unit (GPU), extend to a graphics engine and the like, utilized to generate output images to a display 224. Graphics card(s) 222 can include support for programmable shaders and the like which can manipulate vertices and textures pixel by pixel when rendering output for display 224.

Identity sensor 232 can also be included in hardware 220. Identity sensor 232 can work in conjunction with computer program product 240 identity detector 248 to correctly identify a specific user 110 associated with computing device 210 for whose visual abnormalities the display 224 rendering compensation in accordance to inventive arrangements disclosed herein can take place. Identity sensor 232 can take the form of, but is not limited to, a "front facing" (i.e., user facing) camera on an electronic consumer device, a biometric sensor (for example, retina scan equipment, finger print pad, etc.), a keypad, an RFID sensor, and the like. Identity sensor 232 may or may not be utilized in one embodiment of the disclosure.

Distance sensor 234, which in various embodiments of the disclosure may or may not be part of hardware 220 can provide additional functionality in conjunction with the computer program product 240 distance detector 250. For example, additional functionality can be such that upon sensing a sustained increasing distance between the display 224 and user 110, the distance sensor 234 engages computer program product distance detector 250 to alter the algebraic transform the graphics engine applies to autocompensate screen rendering for a user's visual abnormalities to additionally add a measure of magnification to compensate for the increasing distance between the user 110 and display 224.

In other words, should a user 110 move further away from the screen (be it a television, computer display, etc.), the system can autocompensate for the increasing distance making it more difficult to view the display and magnify the display's content (e.g., text in a word document, outlook menu, on-screen television guide, and the like). The previous example is not intended to be limiting; other additional functionality utilizing the distance sensor 234 is contemplated.

Distance sensor 234 can be a front facing camera on a computing device, In another embodiment, the distance sensor 234 and identity sensor 232 can be one and the same to determine the suitable profile and vision for display: for example, a front facing camera on an electronic consumer device can be utilized to automatically determine not only distance from measuring the size of the object in a picture taken by the front facing camera but also user identity utilizing biometric/face recognition software.

It should be noted that this dynamic adjustment capability is not necessary in all embodiments. In many situations the consumer electronic device 210 is positioned at a relatively stationary distance from user 110 (e.g., a television is very seldom moved from its position relative to the couch, a computer is generally a rather stationary distance from an individual in his or her desk chair, etc.). Furthermore, users with less than 20×20 vision (what is considered normal vision) are used to having to adjust their position relative to a device's display to experience the "best" viewing experience.

The computer program products 240 of computing device 210 can include an operating system 242, one or more applications executing on top of the operating system, firmware, and the like. As discussed in FIG. 1, in one embodiment of the disclosure the algebraic transform to autocompensate for a user's specific visual abnormalities can be implemented in firmware based or kernel level code. This also allows devices that do not inherently have an operating system to implement the linear algebraic transform to perform rendering adjustments for images displayed on the device's screen in accordance with an embodiment of the disclosure.

In one embodiment, a set of user specific settings 244 that contain user specific autocompensation rendering adjustments desired, including user specific goggles settings 246, can be established. These customized adjustments can, in one embodiment, be entered as a conventional corrective lens prescription that a user may have obtained from his or her ophthalmologist.

In another embodiment, a sliding scale for the most common eye disorders including, but not limited to, conditions such as near-sightedness, far-sightedness, and astigmatism, can be implemented allowing a user a more fluid control mechanism. This can be beneficial for users who are either unaware of their exact measure of eye disorder as defined by a prescription, or wish to adjust their known customization parameters one way or another for comfort which can change gradually over time.

Configuration screen 250 shows one, non-limiting, example of a screen through which a user can modify user settings 248, including screen goggles settings specific to the user's desired rendering adjustment to images output to the display 224. As shown in screen 260, a few contemplated settings, which are intended to be illustrative and not exhaustive, for rendering adjustment are shown in rendering adjustment settings section 270. One setting 272 can permit a user to save his or her entered preferences to be saved to his or her current user profile to make settings available upon next log in.

Another setting 274 can permit the saved settings to be made available to devices connected to a network. Additional options 276 for this setting can allow a user to decide to select what types of devices or what specific devices (e.g., only televisions or only John's cellphone, etc.) can access the saved settings; another option for network access is that a user can decide to store his or her rendering adjustment settings in a separate screen goggles server to make access to these settings available to remote devices (e.g., airplane user specific televisions, library computers, etc.). Other options contemplated are to allow a user to selectively enable or disable identity and/or distance detectors when the computing device 210 includes the hardware and computer program product for these applications.

The configurable option for entering rendering adjustment magnitude 280 can permit a user to enter his or her specific preferences. The options are intended to be illustrative and not exhaustive. For example, option 282 allows a user to enter his or her exact corrective lens prescription as received by his or her ophthalmologist. Option 282 can be extended with additional user-selectable parameters such as but not limited to menu 283, which can allow a user to select which entered prescription measure to compensate for should the device not be 3D capable or should the user desire to view the screen without 3D glasses: contemplated options for this selection can be to adjust for the higher/stronger prescription, to adjust for the right eye, or to adjust for the left eye. In another embodiment, the system can provide a default selection of which entered eye prescription to adjust for. In yet another embodiment the user can decide to enter only one eye's prescription measures.

Option 284, on the other hand, can allow for a more fluid or flexible rendering adjustment preference input on a set of sliding scales or dials for each eye (when called for in 3D capable devices) and the most common eye conditions (e.g., myopia, hyperopia, astigmatism, etc.). A plus sign and minus sign can be used to represent hyperopia, presbyopia or myopia (as would be in a spectacles prescription) along with the contemplated sliding scale or dial to represent a magnitude from low to high or 0.00 (indicating perfect 20×20 vision to, for example, 4.0 (considered legally blind) or higher. Another separate option 286 for entering options for 3D capable devices can also be included in the configuration screen for user goggle settings 260.

Figure 3:
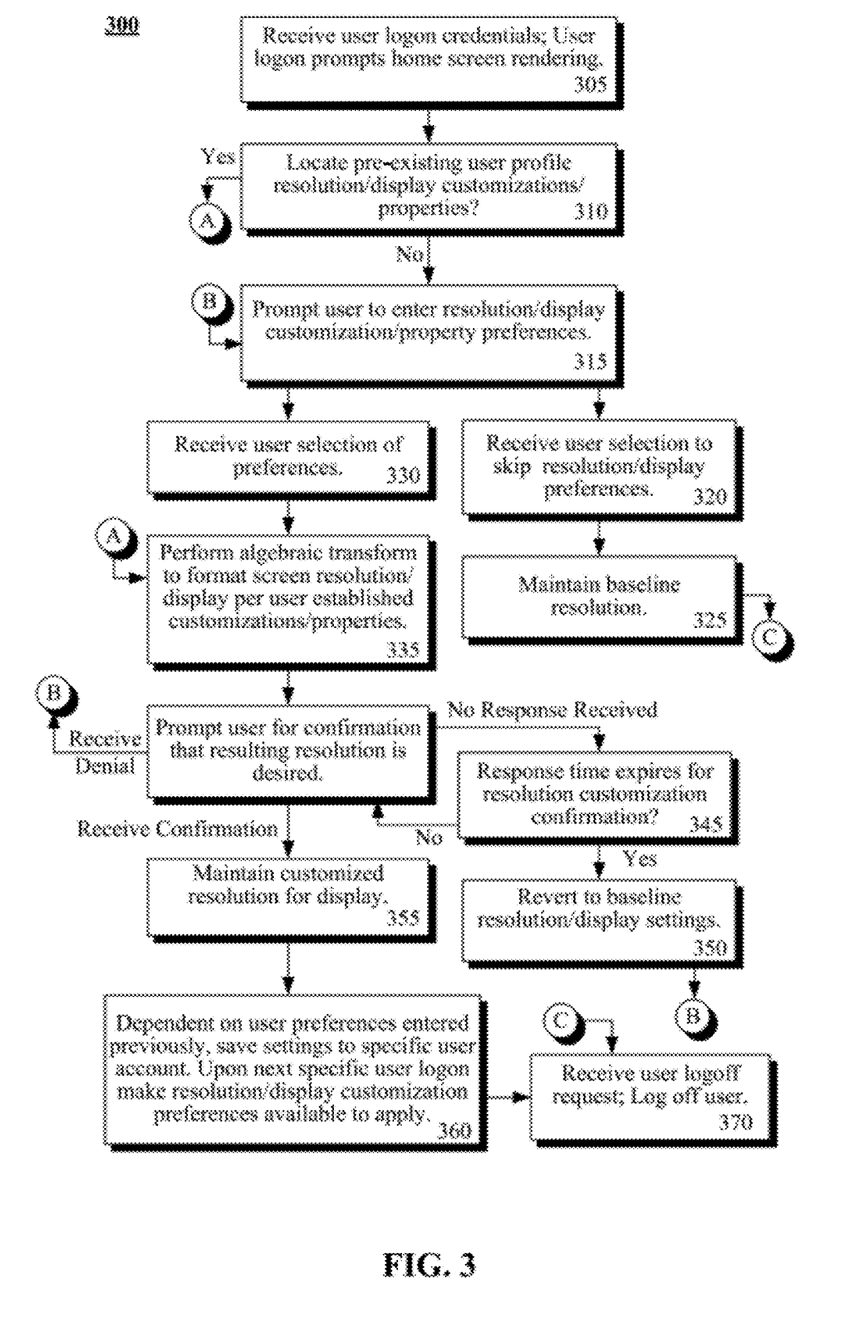
FIG. 3 shows a flowchart of a method from a device perspective through which an embodiment of the disclosure adjusts the digital screen resolution to compensate for the user specific visual abnormality.

FIG. 3 shows a flowchart of a method 300 from a device perspective through which an embodiment of the disclosure adjusts the digital screen resolution to compensate for the user specific visual abnormality. The flowchart shows a set of steps (steps 305-370) that can occur in accordance with the inventive arrangements disclosed herein to administer customized screen resolution settings that can allow a viewer with a common eye disorder to view the digital screen being altered with 20×20 vision without the aid of corrective lenses.

In step 305 the device can receive user logon credentials, which in turn can prompt the user's home screen rendering. User credentials can be, for example, name and password combination, an RFID signal, biometric credentials (including but not limited to fingerprints, retinal scans, voice recognition, face recognition, and the like), a combination of the aforementioned, etc. A home screen can depend on the user device; in this specific embodiment described, a home screen can be the Windows desktop containing application icons, tray bar, start menu, etc.

Upon successful user logon in step 305, in the next step 310 a check for a pre-existing user profile for resolution preferences for display rendering customization properties can be performed. In the case that such settings do pre-exist, the device can then move onto step 335(A) and can apply the pre-existing saved user preferences for customized screen resolution rendering. If, on the other hand, no such pre-existing user profile is found that would present customization preferences for the specifically logged on user, the system can progress to the next step 315.

In step 315 the device can prompt the logged on user to enter his or her preferred resolution display customization settings. These settings can include spectacle prescriptions entered into a GUI along with further options that can include whether or not to save the profile to the currently logged on user account, whether or not to make these rendering adjustment settings available to other devices via a network that the presently utilized consumer device may or may not be currently connected to, specifics for 3D capable device preferences, and the like.

In step 320, the device can receive a user selection to skip entering rendering adjustment preferences. This could be selected by a user wishing to continue to wear his or her corrective lenses for the specific device in question (for example, if the user is at the time of the rendering adjustment prompt is wearing contact lenses, he or she may wish to delay entering customization preferences until a later time or date) or a user who does not suffer from any visual abnormalities and as such would rather not engage in utilizing the system for rendering adjustment to auto compensate for visual abnormalities.

In step 325, after the user has selected to skip entering rendering adjustment parameter preferences the device can maintain the device's display baseline resolution. This screen resolution can be maintained (unless the user manually selects to change resolution settings by either utilizing screen display options inherent to the computing device's screen or the user opens the rendering adjustment GUI to implement rendering adjustments) until a user logoff request is received in step 370(C).

If however, after step 315, instead of receiving a user command to skip entering preferences but rather in step 330 the device receives a set of user preferences selected to auto compensate for the user's specific visual abnormalities, the process can continue to step 335.

In step 335 the device performs an algebraic transform through which the device screen is rendered in a formatted way compensating for the user established visual abnormalities. In essence, the algebraic transform applies the inverse of a Lensmaker's Equation to bend the light coming off of the screen in such a way as a glass lens would to correctly focus the image displayed on the back of the device user's retina.

In step 340, the device can prompt the user to either confirm or deny that the rendering adjustments implemented in the previous step 335 resulted in the desired autocompensation for the user's specific visual abnormalities. Should the device receive no response initially, in step 340 it can continue to prompt the user for a decision on the presented screen rendering adjustment and in step 345 can wait for a response until a predetermined response time expires. Upon the expiration of the response time (with no user selection received) in step 350 the device can revert to the baseline resolution/display settings and can move to step 315(B) during which it can display the prompt to the user to enter rendering customization preferences.

Similarly, should the device (within the allotted response time) receive a user dismissal (denial) of the currently displayed rendering settings in response to step 340's prompt, the process can revert to step 315(B) to allow the user to make any desired changes to the previously entered preferences. If, on the other hand, in response to step 340 prompt a confirmation of the desired user customization settings having been applied is received, in step 355 the customized rendering resolution for the device's display can be maintained.

In step 360, the system can cause the rendering adjustments selected specific to the currently logged on user to be saved to the current user profile. Upon the specific user's next logon the saved rendering adjustment preferences can be made available for application to the display. The customized resolution (unless manually changed by the user during computing) can be maintained until, in step 370(C) the device receives a user logoff request and logs off the user's session.

Figure 4:
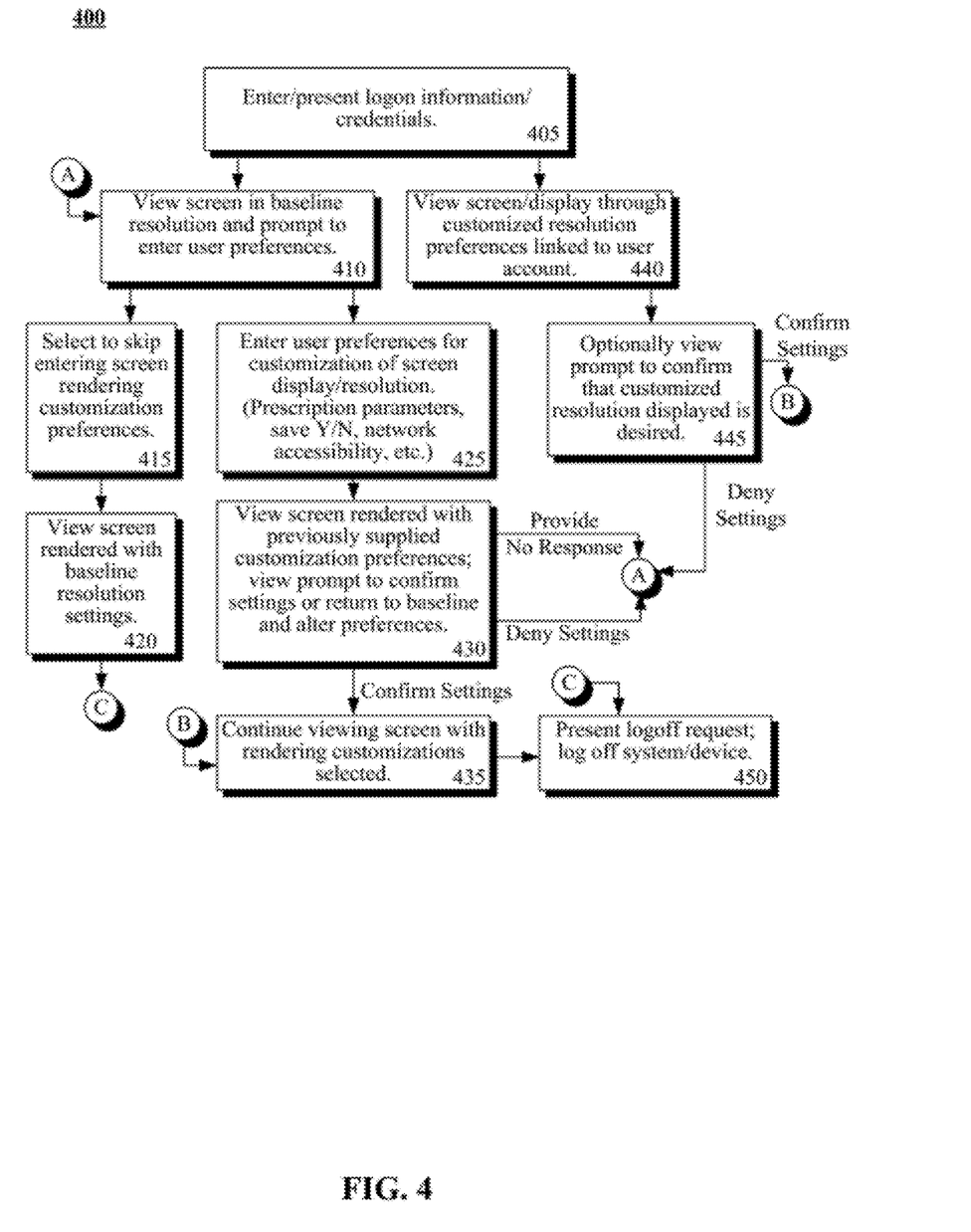
FIG. 4 shows a flowchart of a method from a user perspective through which an embodiment of the disclosure adjusts the digital screen resolution to compensate for the user specific eye disorder.

FIG. 4 shows a flowchart of a method 400 from a user perspective through which an embodiment of the disclosure adjusts the digital screen resolution to compensate for the user specific eye disorder.

The flowchart shows a set of steps (steps 405-450) that can occur in accordance with the inventive arrangements disclosed herein to administer customized screen resolution settings that can allow a viewer with a common eye disorder to select rendering adjustments that can allow him or her to view the digital screen being altered with 20×20 vision without the aid of corrective lenses.

In step 405, the user enters or presents his or her logon information or credentials. As previously discussed, these credentials can take a variety of forms, for example name and password combination, an RFID signal, biometric credentials (including, but not limited to, fingerprints, retinal scans, voice recognition, face recognition, and the like), or a combination of the aforementioned, etc. This list is not intended to be limiting and other logon options are enabled herewith.

In step 410(A), the user can view the screen in the format of the baseline resolution and a prompt to enter user desired customized rendering adjustment preferences. This step can occur, for example, upon a user's first logon to a device outfitted with the autocompensation rendering system for user visual abnormalities. The step can also occur, for example, due to a user's previous decision to delay entering adjustments until a later time and/or date. Other possibilities exist and the previously discussed situations are not intended to present an exhaustive list of reasons for a user to be presented with a baseline resolution rendered display upon logon.

In step 415 the user can select to skip entering screen rendering customization preferences. This can lead to step 420 during which the user views the device's display rendered with the baseline resolution settings. This can be the case (unless the user manually changes the rendering settings during session use) until the user, in step 450(C) presents a logoff request and logs off the system or device.

If, however, after step 410(A), the user in step 425 enters user preferences for the customization of screen rendering adjustments (including but not limited to, for example, prescription parameters for spectacles or contacts, whether or not to save the entered settings to the user's current profile, whether or not to make the saved settings available to other electronic consumer devices via a network, etc.), the user's computing experience can then move into step 430.

In step 430 the user can view the screen rendered with the in step 425 previously supplied rendering customization preferences and can view a prompt to either confirm and accept or deny and decline the display post rendering adjustments. A decline (denial of settings) can lead the user's experience to return to step 410(A) and viewing the screen in baseline resolution settings and allow the user to alter the previously supplied preference parameters. Similarly, providing no response to the prompt of step 430, after a response time out, the user experience can return to step 410(A) to allow the user to adjust or enter user preferences for rendering adjustments.

If the user decides to accept the rendering adjustments presented in step 430, he or she, in step 435(B) can continue to view the device's display rendered with the adjustment parameters entered in step 425. This display setting can be maintained (unless manually changed by the user during use) until, in step 450, the user presents a log off request and logs off the system or device.

In case there are pre-existing rendering adjustment settings for autocompensating for the specific user that is logging on in step 405, in step 440 the user can view the screen or display rendered through the customized resolution preferences linked to the user account directly after logging onto the device.

In step 445, the user can optionally view a prompt that can allow him or her to confirm or deny that the customized resolution displayed is as desired for the session. Confirming the current display rendering settings can lead to step 450(B) where the user can continue to view the screen with these accepted settings until a logoff is requested in step 460. Denying that the pre-existing settings render the device's display as desired can lead to step 410(A) allowing the user to adjust the settings to his or her preference. Again, as discussed, the rendering adjustments can stay in effect until a user logoff occurs in step 450.

Figure 5:
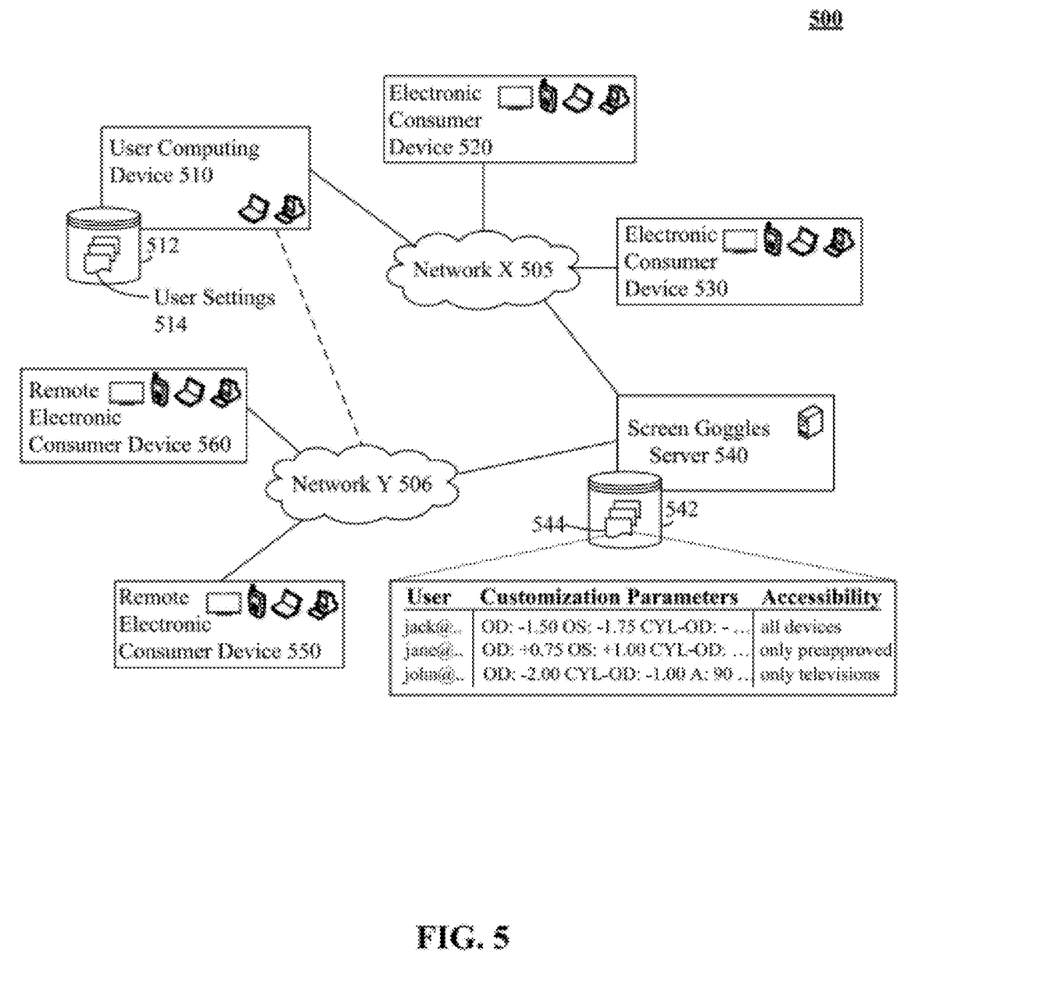
FIG. 5 shows a schematic diagram of a system for use of screen rendering adjustments in accordance with an embodiment of the inventive arrangements disclosed herein.

FIG. 5 shows a schematic diagram of a system 500 for use of screen rendering adjustments in accordance with an embodiment of the inventive arrangements disclosed herein. The system 500 represents an illustrative system for implementing the processes of FIGS. 3 and 4 and the arrangements of FIGS. 1 and 2. System 500 is not to be construed as limiting, and other arrangements and derivatives are contemplated.

A user computing device 510 can be connected to various other electronic consumer devices 520 and 530 as well as screen goggles server 540 via network X 505. FIG. 5 also shows network Y 506 connecting screen goggles server 540 and remote electronic devices 550, 560 and optionally connect to the originating user computing device 510. User computing device 510 can include a database 512 to maintain user settings 514 (such as but not limited to rendering customization preferences, background preferences, sound preferences, and the like). The screen goggles server 540 can include a database 542 which can maintain user display rendering adjustment preference records 544.

Each record 544 linked to a specific user can include attributes such as customization parameters (in the form of spectacle prescriptions that are complete, or partially complete—listing only one eye's prescription in a case where both eyes are subject to a very similar level and type of visual abnormality) and accessibility parameters (who and what devices may have access to the preferences, etc.). The listed attributes are not intended to be a complete listing and other attributes are hereby contemplated.

Utilizing network X 505, user computing device 510 can "share" user settings 514 maintained in database 512 if permitted to do so by the user. In one embodiment, electronic consumer devices with digital displays that are capable of being connected to network X 505 (such as televisions, tablet PCs, smartphones, laptops, desktops, receivers, and the like) can access a user's screen rendering adjustment preferences stored on database 512 of the user computing device 510. Devices 520 and 530 can then implement the previously user provided rendering adjustment preferences autocompensating for the user's visual abnormalities 514 retrieved from computing device's 510 database 512.

In another embodiment, this user preference sharing may be expanded beyond just the home network. For example, network X 505 can be a user's private home network also connecting the user computing device 510 with database 512 for maintaining user settings 514 (including user specific screen rendering adjustment preferences) to a Screen goggles server 540. Screen goggles server 540 can be a machine used to interact with remote electronic consumer devices 550, 560 as well as optionally the preference originating user computing device 510. More specifically, the user computing device 510 may or may not have access to network Y 506 and as such may or not be able to communicate directly with remote electronic consumer devices 550, 560 to offer user specific settings 514 without the use of screen goggles server 540.

In the case of the remote device 550, 560 not having direct access to user settings maintained on the database 512 of device 510, the device may request specific user preferences 544 maintained on database 542 from the screen goggles server 540. A user would have had to previously provided his or her specific display customization preferences to screen goggles server 540 via network X 505 or optionally network Y 506 (should a pathway for this exist). The advantage in using screen goggles server 540 lies in the fact that user computing device 510 with stored user settings/preferences 514 may not be available through network Y 506 at all times to remote device 550, 560.

This can be especially true in a scenario where a user is travelling and accessing a machine at an airport or other hotspot outside of his or her home or work network range. Another scenario can be, for example, the case of a remote devices 550, 560, 560 not having been granted access to network X 505 for various reasons; in this case, the user may still gain access to his or her rendering customization preferences through screen goggles server 540 (with the caveat that the user would have had to provide the server a copy of his or her display customization preferences 544 previously).

The user computing device 510 and electronic consumer devices 520, 530 and remote devices 550, 560 as the devices described in FIGS. 1 and 2, can be any apparatus or device having a display screen capable of having screen resolution adjustments. The computing devices 510, 520, 530 and remote devices 550, 560 can be, but are not limited to, a personal computer, a smart phone, a media player, a consumer electronic device, a kiosk, a gaming system, a navigation system, and the like. Devices 510, 520, 530 and remote devices 550, 560 can be a general purpose computing device able to have its functionality modified by updating or changing installed applications, can be a special purpose computing device designed for a specific set of functionality that is not user modifiable (or minimally so, such as through a firmware upgrade), or can be a device with an intermediate level of user modifiability (i.e., plug-ins or apps can be installed by a user who is otherwise not able to modify core functionality of the device).

Database 512 and 542 can represent data stores able to be physically implemented within any type of hardware including, but not limited to, a magnetic disk, an optical disk, a semiconductor memory, a digitally encoded plastic memory, a holographic memory, or any other recording medium. Data stores 512 and 542 can be a stand-alone storage unit as well as a storage unit formed from a plurality of physical devices. Additionally, information can be stored within data stores 512 and 542 in a variety of manners. For example, information can be stored within a database structure or can be stored within one or more files of a file storage system, where each file may or may not be indexed for information searching purposes. Further, data stores 512 and 542 can utilize one or more encryption mechanisms to protect stored information from unauthorized access.

Networks 505 and 506 can connect computing device 510, electronic consumer devices 520, 530, 550 and 560, server 540, and/or database 542. Network 505 can include any hardware/software/and firmware necessary to convey data encoded within carrier waves. Data can be contained within analog or digital signals and conveyed though data or voice channels. Networks 505 and 507 can include local components and data pathways necessary for communications to be exchanged among computing device components and between integrated device components and peripheral devices. Networks 505, 506 can also include network equipment, such as routers, data lines, hubs, and intermediary servers which together form a data network, such as the Internet. Networks 505, 506 can also include circuit-based communication components and mobile communication components, such as telephony switches, modems, cellular communication towers, and the like. Networks 505, 506 can include line based and/or wireless communication pathways.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:

1. A computer program product for rendering adjustments to images presented on a display, the computer program product comprising a non-transitory computer readable storage medium having computer usable program code embodied therewith, the computer usable program code comprising:
    a linear algebraic transform for matrix manipulation in rendering images to be displayed on a digital screen for electronic consumer devices, said linear algebraic transform comprising a plurality of user-selectable or user provided options, each of the user-selectable or user provided options being associated with a measure of magnitude of the transform desired for various components of the linear algebraic transform, wherein the user-selectable or user provided options comprise user-specific measures of visual abnormalities, wherein said linear algebraic transform utilizes an inverse of a Lensmaker's equation for a viewing user; and computer usable code stored on the non-transitory computer readable storage medium for displaying images on the digital screen, wherein the images result from applying the linear algebraic transform to adjust for visual abnormalities of the viewing user, wherein the visual abnormalities are defined by the Lensmaker's equation.

2. The computer program product of claim 1, wherein said linear algebraic transform being applied to images rendered on a display allows said user to view the digital display in 20×20 vision without the user's corrective lenses.

3. The computer program product of claim 1, said computer usable program code further comprising:

an identity detector for automatically identifying a user having the visual abnormalities for which the linear algebraic transform corrects, wherein the identity detector utilizes input from one of a camera, a biometric sensor, or an RFID sensor to identity the user.

4. The computer program product of claim 1, wherein said electronic consumer device is one of a desktop, laptop, television, tablet, smartphone, digital media player or GPS unit.

5. The computer program product of claim 1 further comprising:

a distance sensor and accompanying software module distance detector configured to detect user distance from the display onto which images are being rendered, wherein upon sensing an increased distance between said user and said display the algebraic transform can be modified to include magnification parameters to magnify said images or partial components of said images being displayed to compensate for said increased distance.

6. The computer program product of claim 1, wherein said linear algebraic transform being applied to images rendered on the digital screen simulates light coming off the digital screen being bent as it would be by corrective lenses to adjust for said user's focal point.

7. A method for adjusting a visual display comprising:

recording, by a processing unit, information for an ocular abnormality of a human in a non-transitory storage medium, wherein said information defines values for a manner in which eyesight of the human varies from an eyesight norm of a general baseline human population;

establishing, by a processing unit, a linear algebraic transform for matrix manipulation in rendering images to be displayed on a digital screen, said linear algebraic transform comprising a plurality of user-selectable or user provided options, each of the user-selectable or user provided options being associated with a measure of magnitude of an adjustment desired for various components of the linear algebraic transform, wherein the user-selectable or user provided options comprise user-specific measures of visual abnormalities, wherein said recorded information comprises the user-specific measures, wherein the linear algebraic transform utilizes an inverse of a Lensmaker's Equation, and wherein the user-specific measures of visual abnormalities defines values for the Lensmaker's Equation;

before presenting visual media on the electronic visual display, applying, by the processing unit, the linear algebraic transform to the visual media, which results in an adaptation of the visual media so that the human with the ocular abnormality is able to view the visual media more clearly; and presenting the visual media after applying the digital signal processing algorithm on the electronic visual display.

8. The method of claim 7, wherein the visual media is a video.

9. The method of claim 7, wherein the visual media is a graphic.

10. The method of claim 7, wherein said linear algebraic transform being applied to images rendered on the electronic visual display simulates light coming off the electronic visual display being bent as it would be by corrective lenses to adjust for an ocular focal point of said human.

11. The method of claim 7, wherein the user-specific measures correspond to a prescription used to make glasses or contacts for the human with the ocular abnormality.

12. The method of claim 7, further comprising:

presenting test visual content on the electronic display in various manners, which are adjustments for different deviations from the eyesight norm;

receiving user input from the human to the presenting of the test visual content that indicates content most easily seen by the human;

generating the information on the ocular abnormality using the user input to the test visual content.

13. A device comprising:

one or more processors;

a digital screen; and one or more non-transitory storage devices storing computer usable program code able to be executed by the one or more processors, the computer usable program code comprising:

a linear algebraic transform for matrix manipulation in rendering images to be displayed on the digital screen, said linear algebraic transform comprising a plurality of user-selectable or user provided options, each of the user-selectable or user provided options being associated with a measure of magnitude of an adjustment desired for various components of the linear algebraic transform, wherein the user-selectable or user provided options comprise user-specific measures of visual abnormalities, wherein said linear algebraic transform utilizes an inverse of a Lensmaker's equation for a viewing user; and computer usable code stored on one of the non-transitory storage devices for displaying images on the digital screen, wherein the images result from applying the linear algebraic transform to adjust for visual abnormalities of the viewing user, wherein the visual abnormalities are defined by the Lensmaker's equation.

14. The device of claim 13, wherein said linear algebraic transform being applied to images rendered on the digital screen allows said user to view the digital screen in 20×20 vision without the user's corrective lenses.

15. The device of claim 13, wherein said computer usable program code further comprising:

an identity detector for automatically identifying a user having the visual abnormalities for which the linear algebraic transform corrects, wherein the identity detector utilizes input from one of a camera, a biometric sensor, or an RFID sensor to identity the user.

16. The device of claim 13, wherein said device is one of a desktop, laptop, television, tablet, smartphone, digital media player, or GPS unit.

17. The device of claim 13 further comprising:

a distance sensor and accompanying software module distance detector configured to detect user distance from the digital screen onto which images are being rendered, wherein upon sensing an increased distance between said user and said digital screen the linear algebraic transform is be modified to include magnification parameters to magnify said images or partial components of said images being displayed to compensate for said increased distance.

18. The device of claim 13, wherein said linear algebraic transform being applied to images rendered on the digital screen simulates light coming off the digital screen being bent as it would be by corrective lenses to adjust for said user's focal point.

\* \* \* \* \*